United States Patent [19]

Lavanish et al.

[11] Patent Number: 5,310,937
[45] Date of Patent: May 10, 1994

[54] 2,5-DIOXO-3-PYRROLINE-1-ACETANILIDE FUNGICIDAL AGENTS AND METHOD FOR THE PREPARATION THEREOF

[75] Inventors: Jerome M. Lavanish, Yardley; Bomi Patel, Philadelphia, both of Pa.

[73] Assignee: American Cyanamid Company, Wayne, N.J.

[21] Appl. No.: 1,970

[22] Filed: Jan. 8, 1993

Related U.S. Application Data

[62] Division of Ser. No. 713,179, Jun. 10, 1991, Pat. No. 5,204,366.

[51] Int. Cl.$^5$ .................................... C07D 207/38
[52] U.S. Cl. .................................... 548/548; 548/544
[58] Field of Search .................... 548/545, 544, 548

[56] References Cited

U.S. PATENT DOCUMENTS 4,927,844  6/1990  Wollweber et al. .............. 514/425

FOREIGN PATENT DOCUMENTS 0382463  8/1990  European Pat. Off. .
617320  5/1980  Switzerland .

OTHER PUBLICATIONS

Zeitschrift Fur Naturforschung, Section C, vol. 40C, No. 7/8, 1985, Tubingen De, pp. 652–656, Huppatz J. L., Casida J. E.
Berichte Der Deutschen Chemischen Gesellschaft, vol. 10, 1967, Weinheim De, pp. 2757–2760, L. Paul, A. Dittmar, C. Rusch.

*Primary Examiner*—David B. Springer
*Attorney, Agent, or Firm*—John W. Hogan, Jr.

[57] ABSTRACT

2,5-Dioxo-3-pyrroline-1-acetanilide compounds which are effective for the control or prevention of phytopathogenic fungi are described. A method for the fungicidal use of said compounds, fungicidal compositions containing said compounds and a method for the preparation of said compounds are also presented.

11 Claims, No Drawings

2,5-DIOXO-3-PYRROLINE-1-ACETANILIDE FUNGICIDAL AGENTS AND METHOD FOR THE PREPARATION THEREOF

This is a divisional of co-pending application Ser. No. 07/713,179 filed on Jun. 10, 1991, now U.S. Pat. No. 5,204,366.

BACKGROUND OF THE INVENTION

Phytopathogenic fungi are the causal agents for many diseases which infect and destroy crops. Even with the wide variety of fungicides available today to combat this problem diseases caused by fungi still abound. Accordingly, there is an ongoing search in the art to create new and more effective fungicides and methods for controlling or preventing fungal infestations.

It is therefore an object of the present invention to provide 2,5-dioxo-3-pyrroline-1-acetanilide compounds that are highly effective for controlling or preventing phytopathogenic fungal infestations in agronomic crops, both growing and harvested.

SUMMARY OF THE INVENTION

The present invention describes 2,5-dioxo-3-pyrroline-1-acetanilide compounds that are useful in the control or prevention of phytopathogenic fungi, the causal agents for diseases infecting agronomic crops, both growing and harvested.

2,5-Dioxo-3-pyrroline-1-acetanilide compounds of the present invention which are useful for the protection of plants from the effects of plant pathogenic fungi, have the structural formula I

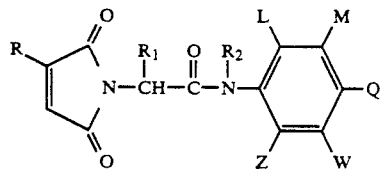

wherein
R is hydrogen, halogen, or $C_1$–$C_4$ alkyl optionally substituted with halogen;
$R_1$ is hydrogen, $C_1$–$C_{10}$ alkyl optionally substituted with $C_1$–$C_9$ alkoxy or halogen, $C_3$–$C_6$ cycloalkyl, $C_2$–$C_{10}$ alkylthioalkyl, $C_4$–$C_{10}$ cycloalkylalkyl, or phenyl or $C_7$–$C_{10}$ phenylalkyl optionally substituted
    with one to three halogen atoms, $C_1$–$C_4$ alkoxy groups, nitro groups, cyano groups, or $C_1$–$C_4$ alkyl groups optionally substituted with halogen;
$R_2$ is hydrogen, or $C_1$–$C_6$ alkyl optionally substituted with $C_1$–$C_5$ alkoxy;
L, M, Q, W and Z are each independently hydrogen, $C_1$–$C_6$ alkyl optionally substituted with $C_1$–$C_4$ alkoxy or halogen, $C_1$–$C_4$ alkoxy, $C_3$–$C_6$ cycloalkyl, $C_2$–$C_6$ alkenyl, $C_5$–$C_6$ cycloalkenyl, $C_2$–$C_6$ alkynyl,
    halogen,
    nitro,
    cyano,
    $CO_2R_3$, or
    phenyl or phenoxy optionally substituted with one to three $C_1$–$C_4$ alkoxy groups, halogen atoms, nitro groups, cyano groups, or $C_1$–$C_4$ alkyl groups optionally substituted with halogen, with the proviso that at most only one of L, M, Q, W or Z may be phenyl or phenoxy;
$R_3$ is $C_1$–$C_4$ alkyl; and when $R_1$ is a substituent other than hydrogen, the optical isomers thereof; and with the proviso that when $R_1$ is sec-propyl and R is hydrogen or methyl, then at least one of L, M, Q, W, or Z must be other than hydrogen.

DETAILED DESCRIPTION OF THE INVENTION

A more preferred group of 2,5-dioxo-3-pyrroline-1-acetanilide compounds of formula I described above are those in which
R is hydrogen or halogen;
$R_1$ is hydrogen, $C_1$–$C_{10}$ alkyl, or $C_7$–$C_{10}$ phenyl alkyl optionally substituted on the phenyl ring with one to three halogen atoms, $C_1$–$C_4$ alkoxy groups, nitro groups, cyano groups, or $C_1$–$C_4$ alkyl groups optionally substituted with halogen;
$R_2$ is hydrogen or $C_1$–$C_6$ alkyl;
L, M, Q, W and Z are each independently hydrogen, $C_1$–$C_6$ alkyl optionally substituted with $C_1$–$C_4$ alkoxy or halogen, $C_1$–$C_4$ alkoxy, $C_3$–$C_6$ cycloalkyl, halogen, nitro, cyano, $CO_2R_3$, or phenyl or phenoxy optionally substituted with one to three $C_1$–$C_4$ alkoxy groups, halogen atoms, nitro groups, cyano groups, or $C_1$–$C_4$ alkyl groups optionally substituted with halogen with the proviso that at most only one of L, M, Q, W, or Z may be phenyl or phenoxy;
$R_3$ is $C_1$–$C_4$ alkyl; and with the proviso that when $R_1$ is sec-propyl and R is hydrogen, then at least one of L, M, Q, W, or Z must be other than hydrogen.

A most preferred group of formula I compounds especially useful in the control or prevention of phytopathogenic fungi are those in which
R is hydrogen;
$R_1$ is hydrogen, $C_1$–$C_{10}$ alkyl, or $C_7$–$C_{10}$ phenylalkyl optionally substituted on the phenyl ring with one to three halogen atoms;
$R_2$ is hydrogen or $C_1$–$C_6$ alkyl;
L, M, Q, W and Z are each independently hydrogen, $C_1$–$C_6$ alkyl optionally substituted with $C_1$–$C_4$ alkoxy or halogen, $C_1$–$C_4$ alkoxy, $C_3$–$C_6$ cycloalkyl, halogen, nitro, cyano, $CO_2R_3$, phenyl or phenoxy; and
$R_3$ is $C_1$–$C_4$ alkyl.

By the term halogen we intend an atom selected from the group consisting of F, Cl, Br and I.

The present invention also provides a method for controlling or preventing phytopathogenic fungi by applying to the locus of the fungi a fungicidally effective amount of a compound having the structural formula I

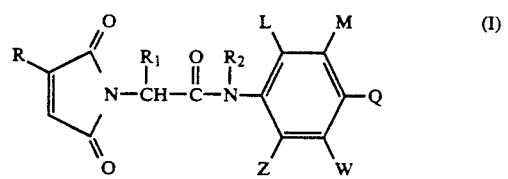

wherein
R is hydrogen, halogen, or $C_1$–$C_4$ alkyl optionally substituted with halogen;
$R_1$ is hydrogen, $C_7$–$C_{10}$ alkyl optionally substituted with $C_1$–$C_9$ alkoxy or halogen, $C_3$–$C_6$ cycloalkyl, $C_2$–$C_{10}$ alkylthioalkyl, $C_4$–$C_{10}$ cycloalkylalkyl, or phenyl or $C_7$–$C_{10}$ phenylalkyl optionally substituted with one to three halogen atoms, $C_1$–$C_4$ alkoxy groups, nitro groups, cyano groups, or $C_1$–$C_4$ alkyl groups optionally substituted with halogen;

$R_2$ is hydrogen, or $C_1$-$C_6$ alkyly optionally substituted with $C_1$-$C_5$ alkoxy;

L, M, Q, W and Z are each independently hydrogen, $C_1$-$C_6$ alkyl optionally substituted with $C_1$-$C_4$ alkoxy or halogen, $C_1$-$C_4$ alkoxy, $C_3$-$C_6$ cycloalkyl, $C_2$-$C_6$ alkenyl, $C_5$-$C_6$ cycloalkenyl, $C_2$-$C_6$ alkynyl,
halogen,
nitro,
cyano,
$CO_2R_3$, or
phenyl or phenoxy optionally substituted with one to three $C_1$-$C_4$ alkoxy groups, halogen atoms, nitro groups, cyano groups, or $C_1$-$C_4$ alkyl groups optionally substituted with halogen, with the proviso that at most only one of L, M, Q, W or Z may be phenyl or phenoxy;

$R_3$ is $C_1$-$C_4$ alkyl; and when $R_1$ is a substituent other than hydrogen, the optical isomers thereof; and with the proviso that when $R_1$ is sec-propyl and R is hydrogen or methyl, then at least one of L, M, Q, W, or Z must be other than hydrogen.

A more preferred method for controlling or preventing phytopathogenic fungi is that in which R is hydrogen or halogen;

$R_1$ is hydrogen,
$C_1$-$C_{10}$ alkyl, or
$C_7$-$C_{10}$ phenyl alkyl optionally substituted on the phenyl ring with one to three halogen atoms, $C_1$-$C_4$ alkoxy groups, nitro groups, cyano groups, or $C_1$-$C_4$ alkyl groups optionally substituted with halogen;

$R_2$ is hydrogen or $C_1$-$C_6$ alkyl; L, M, Q, W and Z are each independently hydrogen, $C_1$-$C_6$ alkyl optionally substituted with $C_1$-$C_4$ alkoxy or halogen, $C_1$-$C_4$ alkoxy, $C_3$-$C_6$ cycloalkyl,
halogen,
nitro,
cyano,
$CO_2R_3$, or phenyl or phenoxy optionally substituted with one to three $C_1$-$C_4$ alkoxy groups,
halogen atoms,
nitro groups,
cyano groups, or
$C_1$-$C_4$ alkyl groups optionally substituted with halogen with the proviso that at most only one of L, M, Q, W, or Z may be phenyl or phenoxy;

$R_3$ is $C_1$-$C_4$ alkyl; and with the proviso that when $R_1$ is sec-propyl and R is hydrogen, then at least one of L, M, Q, W, or Z must be other than hydrogen.

A most preferred method for controlling or preventing phytopathogenic fungi is that in which
R is hydrogen;
$R_1$ is hydrogen, $C_1$-$C_{10}$ alkyl, or $C_7$-$C_{10}$ phenylalkyl optionally substituted on the phenyl ring with one to three halogen atoms;
$R_2$ is hydrogen or $C_1$-$C_6$ alkyl;

L, M, Q, W and Z are each independently hydrogen, $C_1$-$C_6$ alkyl optionally substituted with $C_1$-$C_4$ alkoxy or halogen, $C_1$-$C_4$ alkoxy, $C_3$-$C_6$ cycloalkyl, halogen, nitro, cyano, $CO_2R_3$, phenyl or phenoxy; and $R_3$ is $C_1$-$C_4$ alkyl.

The present invention also provides antifungal compositions which include an inert solid or liquid diluent and a compound having the structural formula I described above, except that when $R_1$ is sec-propyl and R is hydrogen or methyl, then L, M, Q, W and Z may all be hydrogen.

A 2,5-dioxo-3-pyrroline-1-acetanilide compound of formula I may be prepared by reacting an amino acid having the structural formula II

wherein $R_1$ is hydrogen, $C_1$-$C_{10}$ alkyl optionally substituted with $C_1$-$C_9$ alkoxy or halogen, $C_3$-$C_6$ cycloalkyl, $C_2$-$C_{10}$ alkylthioalkyl, $C_4$-$C_{10}$ cycloalkylalkyl, or phenyl or $C_7$-$C_{10}$ phenylalkyl optionally substituted with one to three halogen atoms, $C_1$-$C_4$ alkoxy groups, nitro groups, cyano groups, or $C_1$-$C_4$ alkyl groups optionally substituted with halogen;

when $R_1$ is a substituent other than hydrogen, the optical isomers thereof; with at least one molar equivalent of a maleic anhydride of structure III

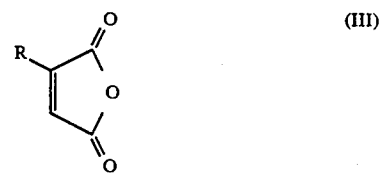

wherein R is hydrogen, halogen or $C_1$-$C_4$ alkyl optionally substituted with halogen and at least one molar equivalent of an acid in the presence of an inert organic solvent to form a N-(carboxymethyl)maleamic acid intermediate of formula IV

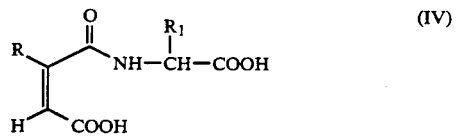

wherein R and $R_1$ are as described above. The formula IV N-(carboxymethyl)maleamic acid is reacted with at least two molar equivalents of an organic base in the presence of an inert organic solvent. Water is concurrently removed from the reaction mixture via azeotropic distillation, molecular sieves, calcium hydride or the like to form the corresponding 2,5-dioxo-3-pyrroline-1-acetate. The acetate is reacted with at least one molar equivalent of a mineral acid to form the 2,5-dioxo-3-pyrroline-1-acetic acid of formula V

wherein R and $R_1$ are as described above. The formula V acetic acid is reacted with at least one molar equivalent of a formula VI aniline

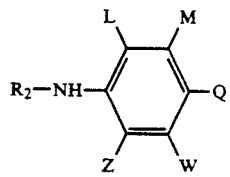

wherein L, M, Q, W, Z and R$_2$ are as described above for formula I and at least one molar equivalent of a coupling agent in the presence of an inert organic solvent to form the desired 2,5-dioxo-3-pyrroline-1-acetanilide compound of formula I. The above reaction scheme is shown below in flow diagram I:

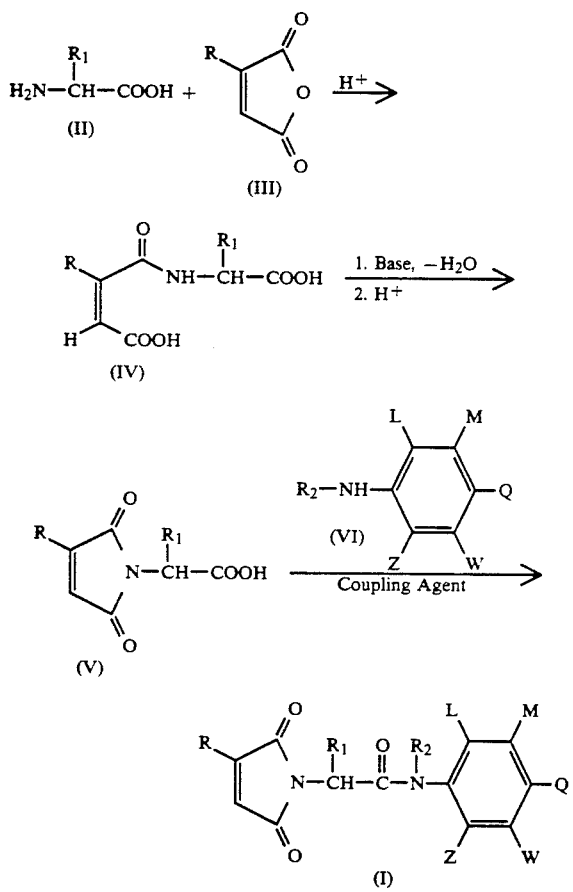

Acids suitable for use in the above reaction scheme include acids such as acetic acid, formic acid, hydrochloric acid, oxalic acid and the like.

Mineral acids useful in the above reaction scheme include mineral acids such as sulfuric acid, hydrochloric acid, nitric acid and the like.

Coupling agents suitable for use in the above reaction include coupling agents such as a p-nitrophenol ester, an N-hydroxysuccinimide, 1-(3-dimenthylaminopropyl)-3-ethyl carbodiimide, dicyclohexylcarbodiimide, an ethyl chloroformate/triethylamine mixture and the like.

A 2,5-dioxo-3-pyrroline-1-acetanilide compound of formula I may also be prepared by reacting the above-prepared formula V 2,5-dioxo-3-pyrroline-1-acetic acid with at least one molar equivalent of thionyl chloride in the presence of an inert aromatic solvent to form the corresponding acid chloride and reacting the acid chloride with at least one molar equivalent of a formula VI aniline and at least one molar equivalent of an organic base in the presence of an inert organic solvent to form the desired compound of formula I. The above reaction scheme is shown below in flow diagram II:

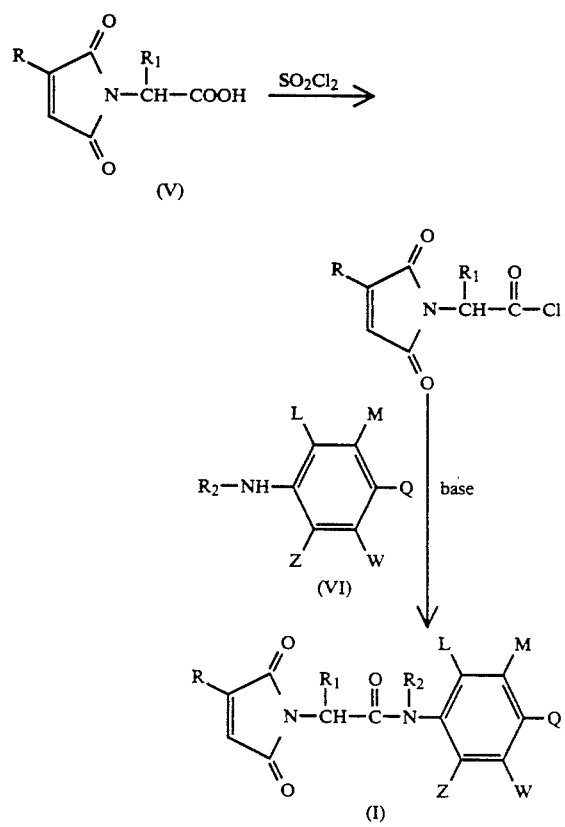

Organic bases suitable for use in the above reaction schemes include organic bases such as C$_1$-C$_4$ trialkylamines, pyridine, dimethylaminopyridine and the like.

Compounds of formula I wherein R$_2$ is C$_1$-C$_6$ alkyl optionally substituted with C$_1$-C$_5$ alkoxy may be prepared from their formula I precursor wherein R$_2$ is hydrogen by reacting said precursor with the appropriate alkylhalide in the presence of a base as shown in flow diagram III:

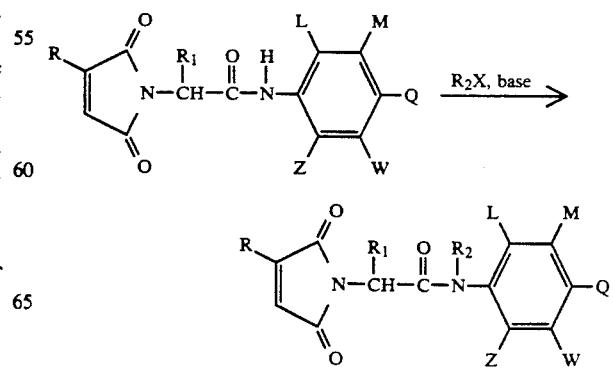

wherein $R_2$ is $C_1$-$C_6$ alkyl optionally substituted with $C_1$-$C_5$ alkoxy and X is halogen.

The compounds of the present invention are effective for controlling or preventing the growth of phytopathogenic fungi in the presence of growing or harvested plants when applied to said plants at fungicidally effective rates. This will vary somewhat with the virulence of the pathogen in question and with other factors such as the environment in which treatment is conducted. These compounds are especially useful for the control of Plasmpara viticola, the causal agent of grape downy mildew. Certain compounds of the invention may not only be employed to control fungi that have infected plants, but also may be applied to healthy plants or seeds or to the soil in which the plant is to be grown in order to prevent infestation.

To protect plants from phytopathogenic fungi, the compounds of formula I are applied to the foliage of the plant, to the seed of the plants, or to the soil in which the plant grows or is to be grown, in the form of a liquid, preferably in aqueous spray, or dust, or granular formulation. Solutions or suspensions containing from about 20 ppm to about 1,000 ppm, and preferably 50 ppm to 500 ppm, of formula I compounds are generally effective for this use.

The compounds of the invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with inert, solid or liquid diluents.

For example, wettable powders, dusts, and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical flowable liquid can be prepared by admixing about 30% to 90% by weight of a gelling agent such as bentonite, 2% to 5% by weight of a dispersing agent such as sodium lignosulfonate, about 1% by weight of polyethyleneglycol, and about 40% to 60% by weight of water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

It is understood that the compounds of the present invention can be applied singly or in combination with one or more other fungicidal compounds, such application being made either by combination of the fungicidal compounds or their formulations in a common container prior to use or by sequential application of the active fungicidal compounds or their formulations to the host crop or its environment. Compounds suitable for combination with the compounds of this invention are suggested by, but not limited to, the following: 4,6-dinitro-o-cresol, benalaxyl, benomyl, captafol, captan, carbendazim, chlorothalonil, copper, cymoxanil, dichlobutrazole, dichlofluanid, diethofencarb, difenconazole, dimethomorph, diniconazole, dinocap, dithianon, fenarimol, fentin acetate, ferbam, flusilazole, folpet, fosetyl, hexaconazole, imazalil, iprodione, mancopper mancozeb, maneb, mepronil, mercuric oxide, metalaxyl, metiram, myclobutanil, nuarimol, ofurace, oxadixyl, penconazole, pencyuron, phosphorous acid, procymidone, propineb, pyrifenox, quintozene, sodium arsenite, sulphur, thiabendazole, thiophanate methyl, thiram, tolclophos-methyl, triadimefon, triadimenol, triforine, vinclozolin, zineb, and ziram.

In order to facilitate a further understanding of the invention, the following examples are presented primarily for the purpose of illustrating more specific details thereof. The invention is not to be deemed limited thereby except as defined in the claims.

EXAMPLE 1

Preparation of L-N-(α-Carboxyphenethyl)maleamic acid

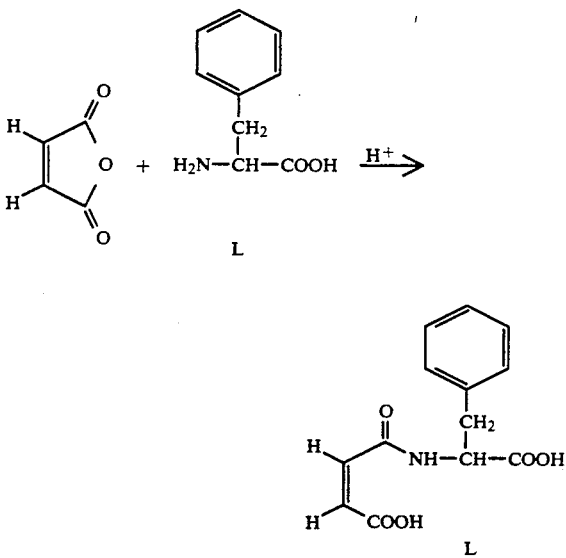

To a suspension of L-phenylalanine (5.1 g, 0.031 mol) dispersed in a mixture of acetic acid and acetone is added a solution of maleic anhydride (3.03 g, 0.031 mol) in acetone. The reaction mixture is heated at about 50° C. for 2½ hours, cooled to room temperature and poured into a mixture of hexane and ethyl acetate. The resultant mixture is filtered to give the title product as a white solid (7.4 g, mp 133° C.), identified by $^1$HNMR, CIMS and IR analyses.

Following the above procedure and using the appropriately substituted glycine and the appropriately substituted maleic anhydride, the formula IV compounds in table I are obtained.

TABLE I

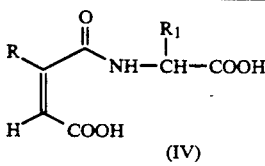

(IV)

| R | $R_1$ | mp °C. | Isomer |
|---|---|---|---|
| H | $CH_2C_6H_5$ | 136–140 | D, L |
| H | p-$ClC_6H_5CH_2$ | 139 | D, L |
| H | m-$ClC_6H_5CH_2$ | 132–134 | D, L |
| H | o-$ClC_6H_5CH_2$ | 124 | D, L |
| Br | H | 114 | — |
| H | H | 187 | — |
| H | $CH(CH_3)_2$ | 140 | D, L |
| H | $CH(CH_3)_2$ | 142 | L |
| H | $CH(CH_3)_2$ | 142 | D |
| H | $CH_3$ | 143 | D, L |
| H | $CH_3$ | 145 | L |
| H | $CH_2CH(CH_3)_2$ | 164 | D, L |
| H | $CH_2CH(CH_3)_2$ | 141 | L |
| H | $CH(CH_3)CH_2CH_3$ | oil | L |

TABLE II

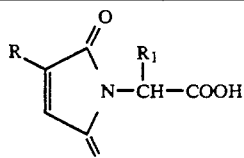

(V)

| R | $R_1$ | mp °C. | Isomer |
|---|---|---|---|
| H | $CH_2C_6H_5$ | 87–90 | D, L |
| H | p-$ClC_6H_5CH_2$ | 145 | D, L |
| H | m-$ClC_6H_5CH_2$ | 151 | D, L |
| H | o-$ClC_6H_5CH_2$ | 130–134 | D, L |
| Br | H | 134 | — |
| H | H | 113 | — |
| H | $CH(CH_3)_2$ | 87 | D, L |
| H | $CH(CH_3)_2$ | 89 | L |
| H | $CH(CH_3)_2$ | oil | D |
| H | $CH_3$ | 97 | D, L |
| H | $CH_3$ | 98 | L |
| H | $CH_2CH(CH_3)_2$ | 102 | D, L |
| H | $CH_2CH(CH_3)_2$ | 87–90 | L |
| H | $CH(CH_3)CH_2CH_3$ | oil | L |

EXAMPLE 2

Preparation of
L-2,5-Dioxo-α-benzyl-3-pyrroline-1-acetic acid

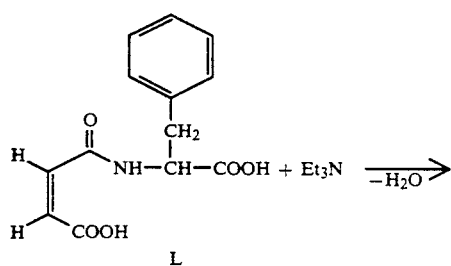

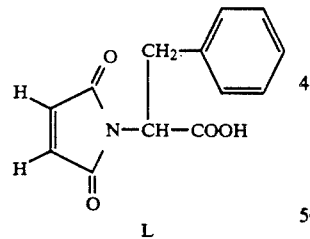

A suspension of L-N-(α-carboxyphenethyl)maleamic acid (7.0 g, 0.027 mol) in toluene is treated with triethylamine (8.1 mL, 0.0532 mol), refluxed for 2 hours using a Dean-Stark trap, cooled to room temperature and concentrated in vacuo to give a yellow oil residue. The residue is dissolved in ethyl acetate and treated with 1N Hydrochloric acid. The mixture is separated, the organic phase is dried over anhydrous sodium sulfate and concentrated in vacuo to yield the title product as a white solid (4.56 g, mp 87° C.), indentified by $^1$HNMR, CIMS and IR analyses.

Following the above procedure, and using the appropriately substituted maleamic acid, the following formula V compounds are obtained and shown in Table II.

EXAMPLES 3–107

Preparation of
L-2,5-Dioxo-α-benzyl-4'-chloro-3-pyrroline-1-acetanilide

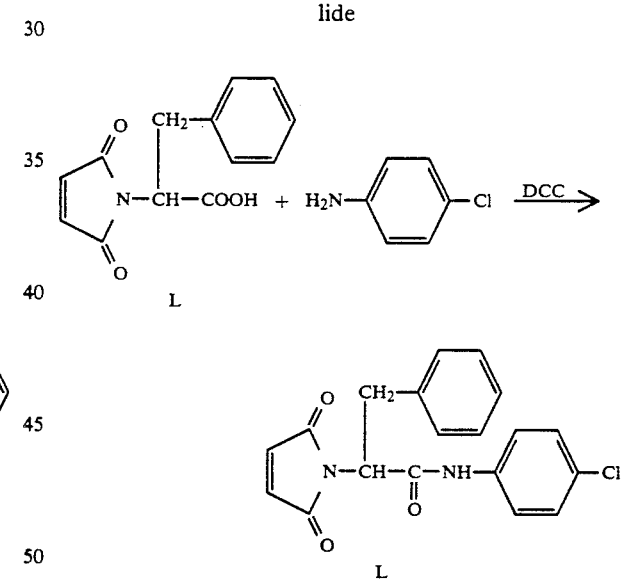

To a solution of L-2,5-dioxo-α-benzyl-3-pyrroline-1-acetic acid (1.5 g, 0.006 mol) in tetrahydrofuran is added a solution of dicyclohexylcarbodiimide (1.38 g, 0.0066 mol) in tetrahydrofuran at room temperature under nitrogen. After stirring for 1 hour, the reaction mixture is treated with a solution of p-chloroaniline (0.78 g, 0.006 mol) in tetrahydrofuran, stirred for 4 hours, filtered and the filtrate is concentrated in vacuo to give a brown oil. Flash chromatography on silica gel (hexane/ethyl acetate - 70/30) gives the title product as a pale yellow solid (2.0 g, mp 189.5° C.), identified by $^1$HNMR, CIMS and IR analyses.

Following the above procedure and using the appropriately substituted 2,5-dioxo-3-pyrroline-1-acetic acid and appropriately substituted aniline, the following formula I compounds in table III are obtained.

TABLE III

| Example | R | R₁ | R₂ | L | M | Q | W | Z | mp °C. | Isomer |
|---|---|---|---|---|---|---|---|---|---|---|
| 4 | H | CH₂C₆H₅ | H | H | H | H | H | H | yellow oil | L |
| 5 | H | CH₂C₆H₅ | H | H | H | OCH₃ | H | H | 119 | L |
| 6 | H | CH₂C₆H₅ | H | H | Cl | H | Cl | H | 158 | L |
| 7 | H | CH₂C₆H₅ | H | OCH₃ | H | H | OCH₃ | H | brown oil | L |
| 8 | H | CH₂C₆H₅ | H | OCH₃ | H | OCH₃ | H | H | oil | L |
| 9 | H | CH₂C₆H₅ | H | H | H | cyclohexyl | H | H | 190 | L |
| 10 | H | CH₂C₆H₅ | H | NO₂ | H | OCH₃ | H | H | orange oil | L |
| 11 | H | CH₂C₆H₅ | H | CH₃ | H | CH₃ | H | H | 142–143 | L |
| 12 | H | CH₂C₆H₅ | H | CH₃ | H | H | H | CH₃ | 153–155 | L |
| 13 | H | CH₂C₆H₅ | H | F | H | F | H | H | 126 | L |
| 14 | H | CH₂C₆H₅ | H | Br | H | Br | H | H | yellow oil | L |
| 15 | H | CH₂C₆H₅ | H | H | F | H | F | H | 121 | L |
| 16 | H | CH₂C₆H₅ | H | H | H | OC₆H₅ | H | H | 140 | L |
| 17 | H | CH₂C₆H₅ | H | Cl | Cl | H | H | H | 164 | L |
| 18 | H | CH₂C₆H₅ | H | Cl | H | Cl | H | H | yellow oil | L |
| 19 | H | CH₂C₆H₅ | H | Cl | H | H | Cl | H | yellow oil | L |
| 20 | H | CH₂C₆H₅ | H | H | H | F | H | H | 144 | L |
| 21 | H | CH₂C₆H₅ | H | H | H | CF₃ | H | H | 169 | L |
| 22 | H | CH₂C₆H₅ | H | H | H | C(CH₃)₃ | H | H | 145 | L |
| 23 | H | CH₂C₆H₅ | H | H | H | CH(CH₃)₂ | H | H | 136 | L |
| 24 | H | CH₂C₆H₅ | H | H | H | CH₂CH₃ | H | H | 132 | L |
| 25 | H | CH₂C₆H₅ | H | H | H | CN | H | H | 147 | L |
| 26 | H | CH₂C₆H₅ | H | H | OCH₃ | OCH₃ | H | H | 121 | L |
| 27 | H | CH₂C₆H₅ | H | H | OCH₃ | H | OCH₃ | H | 128 | L |
| 28 | H | CH₂C₆H₅ | H | CH₃ | H | F | H | H | 137 | L |
| 29 | H | CH₂C₆H₅ | H | CH₃ | H | Cl | H | H | 143 | L |
| 30 | H | CH₂C₆H₅ | H | CH₃ | H | H | H | H | yellow oil | L |
| 31 | H | CH₂C₆H₅ | H | H | H | Cl | H | H | 187 | D, L |
| 32 | H | CH₂C₆H₅ | H | H | H | CH₃ | H | H | 200–202 | D, L |
| 33 | H | CH₂C₆H₅ | H | H | H | F | H | H | 181–183 | D, L |
| 34 | H | CH₂C₆H₅ | H | Cl | H | Cl | H | H | 193 | D, L |
| 35 | H | CH₂C₆H₅ | H | CH₃ | H | CH₃ | H | H | 140–143 | D, L |
| 36 | H | p-ClC₆H₅CH₂ | H | H | H | Cl | H | H | 194–196 | D, L |
| 37 | H | p-ClC₆H₅CH₂ | H | H | H | CH₃ | H | H | 201–202 | D, L |
| 38 | H | p-ClC₆H₅CH₂ | H | Cl | H | Cl | H | H | yellow oil | D, L |
| 39 | H | p-ClC₆H₅CH₂ | H | Br | H | Br | H | H | 244–246 | D, L |
| 40 | H | p-ClC₆H₅CH₂ | H | CH₃ | H | CH₃ | H | H | 172.6 | D, L |
| 41 | H | p-ClC₆H₅CH₂ | H | F | H | F | H | H | 147–148 | D, L |
| 42 | H | mClC₆H₅CH₂ | H | H | H | Cl | H | H | 194 | D, L |
| 43 | H | mClC₆H₅CH₂ | H | H | H | CH₃ | H | H | 204–207 | D, L |
| 44 | H | mClC₆H₅CH₂ | H | Cl | H | Cl | H | H | 197–199 | D, L |
| 45 | H | mClC₆H₅CH₂ | H | CH₃ | H | CH₃ | H | H | 174–176 | D, L |
| 46 | H | mClC₆H₅CH₂ | H | F | H | F | H | H | 155–157 | D, L |
| 47 | H | o-ClC₆H₅CH₂ | H | H | H | Cl | H | H | 191 | D, L |
| 48 | H | o-ClC₆H₅CH₂ | H | H | H | CH₃ | H | H | 199 | D, L |
| 49 | H | o-ClC₆H₅CH₂ | H | H | H | F | H | H | 194–196 | D, L |
| 50 | H | o-ClC₆H₅CH₂ | H | Cl | H | Cl | H | H | 201–203 | D, L |
| 51 | H | o-ClC₆H₅CH₂ | H | CH₃ | H | CH₃ | H | H | yellow oil | D, L |
| 52 | H | o-ClC₆H₅CH₂ | H | F | H | F | H | H | 145 | D, L |
| 53 | Br | H | H | H | H | Cl | H | H | 162–163 | — |
| 54 | H | H | H | H | H | Cl | H | H | 127 | — |
| 55 | H | H | H | H | H | OCH₃ | H | H | 114 | — |
| 56 | H | H | H | H | H | OCH₃ | H | OCH₃ | 168.1 | — |
| 57 | H | H | H | H | OCH₃ | H | H | OCH₃ | 164.2 | — |
| 58 | H | H | H | H | OCH₃ | OCH₃ | OCH₃ | H | 153–154 | — |
| 59 | H | CH(CH₃)₂ | H | H | H | OCH₃ | H | OCH₃ | 141.3 | D, L |
| 60 | H | CH(CH₃)₂ | H | H | H | H | H | H | 105 | D, L |
| 61 | H | CH(CH₃)₂ | H | H | H | H | H | H | yellow oil | L |
| 62 | H | CH(CH₃)₂ | H | H | H | Cl | H | H | yellow oil | L |
| 63 | H | CH(CH₃)₂ | H | H | H | OCH₃ | H | H | yellow oil | L |
| 64 | H | CH(CH₃)₂ | H | H | H | OCH₃ | H | OCH₃ | 144.4 | L |
| 65 | H | CH(CH₃)₂ | H | H | OCH₃ | H | H | OCH₃ | oil | L |
| 66 | H | CH(CH₃)₂ | H | H | H | OCH₃ | OCH₃ | H | 141 | L |
| 67 | H | CH(CH₃)₂ | H | H | OCH₃ | OCH₃ | OCH₃ | H | 154 | L |
| 68 | H | CH(CH₃)₂ | H | H | H | H | H | H | yellow oil | D |
| 69 | H | CH(CH₃)₂ | H | H | H | Cl | H | H | yellow oil | D |
| 70 | H | CH₃ | H | H | H | H | H | H | yellow solid | D, L |
| 71 | H | CH₃ | H | H | H | Cl | H | H | yellow oil | D, L |
| 72 | H | CH₃ | H | H | H | H | Cl | H | 126 | D, L |
| 73 | H | CH₃ | H | H | H | OCH₃ | H | OCH₃ | 124.2 | L |
| 74 | H | CH₃ | H | H | OCH₃ | H | H | OCH₃ | 117.5 | L |
| 75 | H | CH₃ | H | H | H | H | H | H | oil | L |

TABLE III-continued

| Example | R | R₁ | R₂ | L | M | Q | W | Z | mp °C. | Isomer |
|---|---|---|---|---|---|---|---|---|---|---|
| 76 | H | CH₃ | H | H | H | Cl | H | H | oil | L |
| 77 | H | CH₃ | H | H | H | OCH₃ | H | H | yellow oil | L |
| 78 | H | CH₂CH(CH₃)₂ | H | H | H | H | H | H | 138.9 | D, L |
| 79 | H | CH₂CH(CH₃)₂ | H | H | H | Cl | H | H | 171 | D, L |
| 80 | H | CH₂CH(CH₃)₂ | H | H | H | H | H | H | 144.4 | L |
| 81 | H | CH₂CH(CH₃)₂ | H | Cl | H | H | Cl | H | 131 | L |
| 82 | H | CH₂CH(CH₃)₂ | H | Cl | Cl | H | H | H | 88.6 | L |
| 83 | H | CH₂CH(CH₃)₂ | H | H | H | OCH₃ | H | OCH₃ | yellow oil | L |
| 84 | H | CH₂CH(CH₃)₂ | H | H | OCH₃ | H | H | OCH₃ | semi-solid | L |
| 85 | H | CH₂CH(CH₃)₂ | H | H | OCH₃ | OCH₃ | OCH₃ | H | 105.4 | L |
| 86 | H | CH₂CH(CH₃)₂ | H | CH₃ | H | CH₃ | H | H | 124 | L |
| 87 | H | CH₂CH(CH₃)₂ | H | CH₃ | H | CH₃ | CH₃ | H | 138.2 | L |
| 88 | H | CH₂CH(CH₃)₂ | H | F | H | F | H | H | 118 | L |
| 89 | H | CH₂CH(CH₃)₂ | H | Br | H | Br | H | H | oil | L |
| 90 | H | CH₂CH(CH₃)₂ | H | CH₃ | H | OCH₃ | H | H | orange oil | L |
| 91 | H | CH₂CH(CH₃)₂ | H | F | H | F | H | F | oil | L |
| 92 | H | CH₂CH(CH₃)₂ | H | CH₃ | H | H | H | CH₃ | 144.9 | L |
| 93 | H | CH₂CH(CH₃)₂ | H | NO₂ | H | OCH₃ | H | H | orange oil | L |
| 94 | H | CH₂CH(CH₃)₂ | H | OCH₃ | H | NO₂ | H | H | 188.3 | L |
| 95 | H | CH₂CH(CH₃)₂ | H | H | H | cyclohexyl | H | H | 174.4 | L |
| 96 | H | CH₂CH(CH₃)₂ | H | H | OCH₃ | H | OCH₃ | H | yellow solid | L |
| 97 | H | CH(CH₃)CH₂CH₃ | H | H | H | Cl | H | H | 127.7 | L |
| 98 | H | CH(CH₃)CH₂CH₃ | H | H | H | CH₃ | H | H | yellow oil | L |
| 99 | H | CH(CH₃)CH₂CH₃ | H | H | H | F | H | H | 123.5 | L |
| 100 | H | CH(CH₃)CH₂CH₃ | H | F | H | F | H | H | yellow oil | L |
| 101 | H | CH₂CH₂CH₃ | H | H | H | F | H | H | 91.9 | L |
| 102 | H | CH₂CH₂CH₃ | H | Cl | H | Cl | H | H | yellow oil | L |
| 103 | H | CH₂CH₂CH₃ | H | H | H | CH₃ | H | H | yellow oil | L |
| 104 | H | CH₂CH₂CH₃ | H | H | H | Cl | H | H | 128.7 | L |
| 105 | H | CH₂CH₂CH₃ | H | CH₃ | H | CH₃ | H | H | yellow oil | L |
| 106 | H | CH₂C₆H₅ | CH₃ | H | H | CO₂CH₃ | H | H | 182 | L |
| 107 | H | CH₂C₆H₅ | CH₃ | H | H | CH₃ | H | H | 171 | L |

EXAMPLE 108

Preparation of
DL-2,5-Dioxo-α-methyl-3-pyrroline-1-acet-p-anisidide

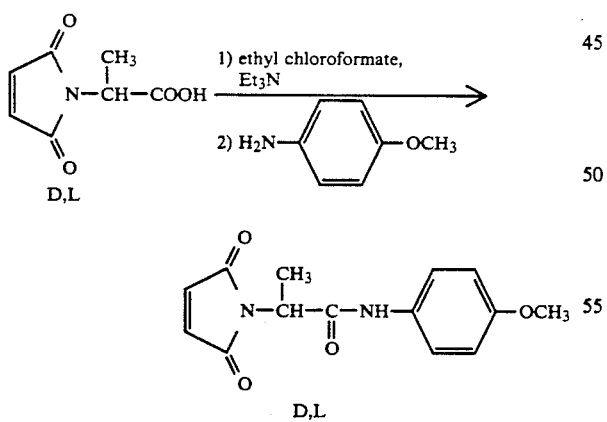

Triethylamine (1.36 mL, 0.0091 mol) and ethyl chloroformate are added dropwise to a solution of DL-2,5-dioxo-α-methyl-3-pyrroline-1-acetic acid (1.5 g, 0.0089 mol) in tetrahydrofuran under nitrogen at 0° C. The reaction mixture is stirred for 10 minutes, treated with p-anisidine (1.09 g, 0.0089 mol), stirred for an additional 2 hours and filtered. Flash chromatography of the filtrate on silica gel (hexane/ethyl acetate - 80/20) gives the title product as a yellow solid (0.74 g, 49%, mp 124° C.), identified by ¹HNMR, CIMS and IR analyses.

EXAMPLES 109–118

Preparation of
DL-2,5-Dioxo-α-methyl-2',4'-dichloro-3-pyrroline-1-acetanilide

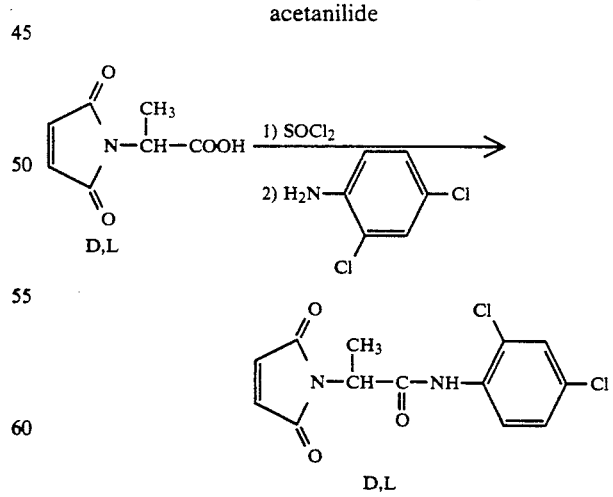

A suspension of DL-2,5-dioxo-α-methyl-3-pyrroline-1-acetic acid (1.5 g, 0.0086 mol) in toluene is treated with thionyl chloride (1.28 mL, 0.0176 mol), warmed to 50° C., stirred for 2½ hours, cooled and concentrated in vacuo to yield a yellow oil. The oil is dissolved in methylene chloride and added to a solution of 2,4-dichloroaniline (1.54 g, 0.0086 mol) and triethylamine (1.32 mL, 0.0094 mol) in methylene chloride under nitrogen at 0° C. The reaction mixture is stirred for 1 hour at room temperature and concentrated in vacuo to give a residue. The residue is flash chromatographed using hexane/ethyl acetate (80/20) as eluent on silica gel to give the title compound as a pale yellow solid (0.94 g, 35%, mp 131° C.), identified by $^1$HNMR, CIMS and IR analysis.

Following the procedure of Example 109, and substituting the appropriate pyrroline-1-acetic acid compound and appropriate aniline, the following formula I compounds in table IV are obtained.

TABLE IV

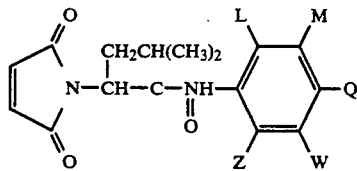

| Example | $R_1$ | L | M | Q | W | Z | mp °C. | Isomer |
|---|---|---|---|---|---|---|---|---|
| 110 | CH$_3$ | Cl | Cl | H | H | H | 130 | D, L |
| 111 | CH$_3$ | Cl | H | H | Cl | H | 130 | D, L |
| 112 | H | H | H | H | H | H | 104 | — |
| 113 | H | Cl | H | Cl | H | H | 136 | — |
| 114 | H | Cl | H | H | Cl | H | 135 | — |
| 115 | H | Cl | H | H | H | Cl | 133 | — |
| 116 | H | Cl | Cl | H | H | H | 134 | — |
| 117 | CH(CH$_3$)$_2$ | H | H | Cl | H | H | 118 | D, L |
| 118 | CH(CH$_3$)$_2$ | H | H | OCH$_3$ | H | H | 158 | D, L |

150.5° C.), identified by $^1$HNMR, CIMS and IR analysis.

Using the above procedure and substituting the appropriate aniline, the following formula I compounds in table V are obtained.

TABLE V

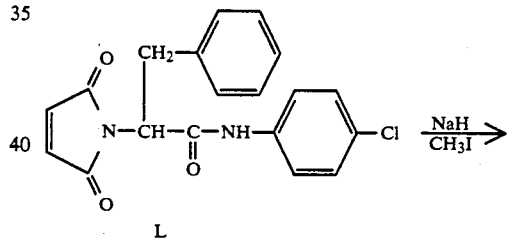

| Example | L | M | Q | W | Z | mp °C. | Isomer |
|---|---|---|---|---|---|---|---|
| 120 | H | H | Cl | H | H | 169.9 | L |
| 121 | H | H | OCH$_3$ | H | H | 114.5 | L |
| 122 | H | H | OCH$_3$ | H | H | 101.9 | D, L |
| 123 | H | Cl | H | Cl | H | 155.4 | L |
| 124 | H | H | H | Cl | Cl | 97.5 | D, L |
| 125 | H | Cl | H | H | Cl | 115.9 | D, L |
| 126 | H | H | Cl | Cl | H | 168.5 | D, L |
| 127 | H | H | Cl | H | Cl | 96.5 | L |
| 128 | H | H | Cl | H | Cl | 119.4 | D, L |
| 129 | H | H | Cl | Cl | H | 205.5 | L |

EXAMPLE 130

Preparation of L-α-benzyl-4′-chloro-N-methyl-2,5-dioxo-3-pyrroline-1-acetanilide

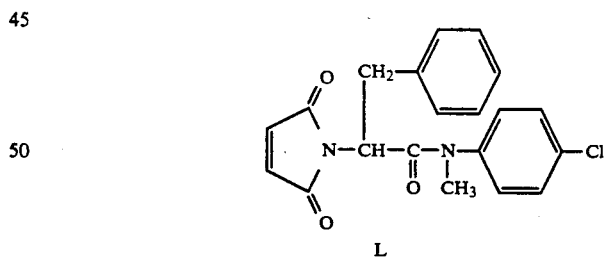

EXAMPLES 119–129

Preparation of DL-2,5-Dioxo-α-isobutyl-3′,5′-dichloro-3-pyrroline-1-acetanilide

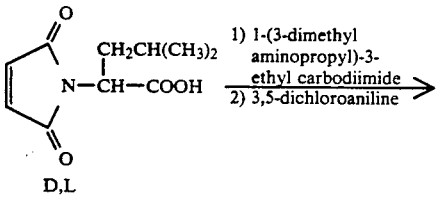

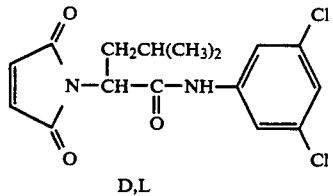

1-(3-Dimethylaminopropyl)-3-ethyl-carbodiimide (3.5 g, 0.0182 mol) is added to a suspension of DL-2,5-dioxo-α-isobutyl-3-pyrroline-1-acetic acid (3.5 g, 0.0166 mol) in tetrahydrofuran. The reaction mixture is stirred for 30 minutes, treated with 3,5-dichloroaniline (2.69 g, 0.0166 mol) under ntirogen, stirred at room temperature for 12 hours and poured into water. The mixture is extracted with methylene chloride. The extracts are combined and concentrated in vacuo to give a residue. Flash chromatography using hexane/ethyl acetate (80/20) as eluent on silica gel of the residue yields the title compound as a pale yellow solid (0.97 g, 16%, mp A solution of L-2,5-dioxo-α-benzyl-4′-chloro-3-pyrroline-1-acetanilide (1.0 g, 0.0028 mol) in tetrahydrofuran is added dropwise to a suspension of sodium hydride (0.11 g, 60% pure, 0.0045 mol) in tetrahydrofuran with stirring under nitrogen at 0° C. After stirring for 1 hour, the reaction mixture is treated with methyl iodide (0.8 g, 0.0056 mol), and stirred for 16 hours and filtered. The filtrate is concentrated in vacuo to give a yellow oil. Flash chromatography of the yellow oil using silica gel and hexane/ethyl acetate (80:20) as eluant gives the title product as a pale yellow solid (0.55 g, mp 181° C.), identified by $^1$HNMR, CIMS and IR analysis.

EXAMPLE 131

Evaluation of test compounds as fungicidal agents

Compounds are dissolved in acetone, diluted to the desired concentration with water and surfactant and sprayed onto the test plants. After drying, the test plants are treated with fungal inoculum. When disease symptom development is optimal plants are rated for disease control. Inoculated untreated plants, solvent/surfactant treated plants and plants treated with a reference standard are used for comparison.

| HEADER | Test Organisms COMMON NAME | SCIENTIFIC NAME |
|---|---|---|
| AS | Apple scab | *Venturia inaequalis* |
| GDM | Grape downy mildew | *Plasmopara viticola* |
| PB | Pepper botrytis | *Botrytis cinerea* |
| RB | Rice blast | *Pyricularia oryzae* |
| SBC | Sugar beet cercospora | *Cercospora beticola* |
| TLB | Tomato late blight | *Phytophthora infestans* |
| WLR | Wheat leaf rust | *Puccinia recondita* f. sp. *tritici* |
| WPM | Wheat powdery mildew | *Erysiphe graminis* f. sp. *tritici* |

Compounds are rated for control of each disease according to the rating scale shown below

| Rating | % Control of Disease |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

The results are reported in table VI.

TABLE VI

| Example No. | AS (400) | GDM (400) | GDM (100) | PB (400) | RB (400) | SBC (400) | TLB (400) | WLR (400) | WPM (400) | (PPM) |
|---|---|---|---|---|---|---|---|---|---|---|
| 3 | 0 | 9 | 8 | 0 | 0 | 0 | 6 | 6 | 0 | |
| 4 | 0 | 0 | | 0 | 0 | 4 | 8 | 0 | 0 | |
| 5 | 0 | 7 | 4 | 0 | 0 | 5 | 5 | 5 | 0 | |
| 6 | 6 | 9 | 9 | 0 | 0 | 4 | 2 | 5 | 0 | |
| 7 | 5 | 9 | 7 | 4 | 6 | 2 | 0 | 7 | 0 | |
| 8 | 0 | 8 | 6 | 6 | 0 | 4 | 0 | 7 | 4 | |
| 9 | 0 | 9 | | 0 | 0 | 0 | 0 | 0 | 0 | |
| 10 | 6 | 9 | 6 | 4 | 0 | 0 | 0 | 7 | 0 | |
| 11 | 7 | 9 | 6 | 6 | 4 | 0 | 4 | 7 | 0 | |
| 12 | 0 | 9 | 7 | 4 | 0 | 0 | 6 | 0 | 0 | |
| 13 | 0 | 9 | 8 | 4 | 0 | 0 | 6 | 0 | 0 | |
| 14 | 7 | 9 | 9 | 7 | 0 | 0 | 0 | 4 | 0 | |
| 15 | 7 | 9 | 9 | 4 | 0 | 0 | 0 | 6 | 0 | |
| 16 | 7 | 9 | 9 | | 0 | 0 | 7 | 4 | 0 | |
| 17 | 8 | 9 | 9 | 0 | 7 | 7 | 0 | 4 | 0 | |
| 18 | 6 | 9 | 9 | 0 | 8 | 7 | 0 | 0 | 0 | |
| 19 | 7 | 9 | 9 | 0 | 9 | 0 | 0 | 0 | 0 | |
| 20 | 9 | 9 | 9 | 0 | 7 | 7 | 8 | 0 | 0 | |
| 21 | 7 | 9 | 9 | 0 | 0 | 0 | 0 | 0 | 0 | |
| 22 | 9 | 9 | 9 | 0 | 7 | 6 | 0 | 0 | 0 | |
| 23 | 9 | 9 | 9 | 0 | 7 | 7 | 0 | 0 | 0 | |
| 24 | 8 | 9 | 9 | 7 | 7 | 7 | 0 | 7 | 0 | |
| 25 | 8 | 9 | 9 | 0 | 7 | 7 | 0 | 7 | 0 | |
| 26 | 6 | 8 | | 2 | 7 | 0 | 0 | 0 | 0 | |
| 27 | 7 | 7 | | 0 | 7 | 0 | 0 | 0 | 0 | |
| 28 | 0 | 9 | 8 | 0 | 0 | 0 | 2 | 0 | 0 | |
| 29 | 7 | 9 | 7 | 7 | 0 | 0 | 2 | 4 | 0 | |
| 30 | 0 | 7 | 0 | 0 | 0 | 4 | 5 | 0 | 0 | |
| 31 | 0 | 6 | | 0 | 4 | 4 | | 0 | 0 | |
| 32 | 0 | 6 | | 0 | 0 | 4 | | 0 | 0 | |
| 33 | 7 | 5 | | 0 | 0 | 0 | 4 | 0 | 0 | |
| 34 | 7 | 9 | 9 | | 6 | 0 | 0 | 4 | 0 | |
| 35 | 7 | 9 | 8 | | 4 | 0 | 0 | 6 | 0 | |
| 36 | 0 | 9 | 8 | 0 | 0 | 0 | 6 | 0 | 0 | |
| 37 | 4 | 9 | 9 | 0 | 0 | 0 | 0 | 0 | 0 | |
| 38 | 8 | 9 | 9 | 0 | 0 | 5 | 4 | 4 | 0 | |
| 39 | 7 | 9 | 8 | 0 | 0 | 6 | 0 | 0 | 0 | |
| 40 | 0 | 9 | 9 | 0 | 0 | 6 | 4 | 0 | 0 | |
| 41 | 8 | 8 | 7 | 0 | 0 | 0 | 6 | 0 | 0 | |
| 42 | 6 | 9 | 9 | 4 | 0 | 6 | 4 | 0 | 0 | |
| 43 | 8 | 9 | 9 | 0 | 0 | 7 | 0 | 0 | 0 | |
| 44 | 7 | 9 | 9 | 4 | 0 | 6 | 4 | 0 | 0 | |
| 45 | 6 | 9 | 6 | 8 | 0 | 7 | 0 | 7 | 0 | |
| 46 | 4 | 9 | 8 | 6 | 0 | 0 | 0 | 7 | 0 | |
| 47 | 4 | 9 | 9 | 0 | 0 | 4 | 2 | 0 | 0 | |
| 48 | 4 | 9 | 9 | 0 | 0 | 0 | 6 | 0 | 0 | |
| 49 | 0 | 9 | 9 | 0 | 0 | 4 | 7 | 0 | 0 | |
| 50 | 7 | 9 | 9 | 0 | 0 | 0 | 0 | 0 | 0 | |
| 51 | 7 | 9 | 7 | 7 | 0 | 7 | 0 | 0 | 0 | |
| 52 | 3 | 9 | 9 | 0 | 0 | 4 | 0 | 0 | 0 | |
| 53 | 0 | 8 | 8 | 0 | 0 | 0 | 7 | 7 | 0 | |
| 54 | 6 | 0 | | 2 | 7 | 6 | 6 | 6 | 0 | |

TABLE VI-continued

| Example No. | AS (400) | GDM (400) | GDM (100) | PB (400) | RB (400) | SBC (400) | TLB (400) | WLR (400) | WPM (400) | (PPM) |
|---|---|---|---|---|---|---|---|---|---|---|
| 55 | 0 | 3 |   | 0 | 9 | 4 | 0 | 5 | 2 |   |
| 56 | 0 | 8 | 7 | 4 | 6 | 6 | 0 | 7 | 0 |   |
| 57 | 0 | 9 | 6 | 7 | 4 | 5 | 7 | 6 | 2 |   |
| 58 | 0 | 8 |   | 4 | 6 | 5 | 6 | 7 | 0 |   |
| 59 | 0 | 7 | 3 | 7 | 4 | 5 | 3 | 6 | 0 |   |
| 60 | 4 |   |   | 2 | 5 | 9 | 1 | 5 | 4 |   |
| 61 | 0 | 6 | 0 | 0 | 0 | 4 | 0 | 4 | 0 |   |
| 62 | 4 | 8 | 0 | 0 | 0 | 0 | 0 | 6 | 0 |   |
| 63 | 0 | 6 | 7 | 0 | 0 | 0 | 0 | 6 | 0 |   |
| 64 | 0 | 9 | 4 | 3 | 4 | 6 | 4 | 7 | 0 |   |
| 65 | 6 | 9 | 6 | 7 | 4 | 6 | 0 | 7 | 0 |   |
| 66 | 0 | 5 | 3 | 3 | 7 | 6 | 0 | 7 | 0 |   |
| 67 | 0 | 0 | 4 | 4 | 6 | 5 | 4 | 7 | 0 |   |
| 68 | 5 | 9 | 8 | 4 | 0 | 5 | 0 | 7 | 0 |   |
| 69 | 3 | 9 | 7 | 4 | 0 | 0 | 0 | 6 | 0 |   |
| 70 | 0 | 8 | 4 | 0 | 7 | 2 | 5 | 7 | 2 |   |
| 71 | 0 | 7 | 5 | 1 | 7 | 0 | 6 | 2 | 0 |   |
| 72 | 6 | 8 | 8 | 0 | 0 | 7 | 7 | 5 | 0 |   |
| 73 | 0 | 0 |   | 5 | 4 | 6 | 4 | 6 | 1 |   |
| 74 | 5 | 8 | 4 | 3 | 4 | 4 | 0 | 7 | 0 |   |
| 75 | 0 | 9 | 3 | 0 | 7 | 0 | 6 | 3 | 0 |   |
| 76 | 3 | 0 |   | 0 | 0 | 7 | 6 | 7 | 0 |   |
| 77 | 0 | 4 | 0 | 0 | 0 | 7 | 0 | 0 | 0 |   |
| 78 | 7 | 7 | 7 | 0 | 6 | 0 | 0 | 6 | 0 |   |
| 79 | 7 | 8 | 7 | 0 | 0 | 0 | 0 | 5 | 0 |   |
| 80 | 7 | 9 | 8 | 4 | 0 | 0 | 4 | 6 | 0 |   |
| 81 | 6 | 0 | 0 | 0 | 0 | 0 | 0 | 0 | 0 |   |
| 82 | 9 | 9 | 8 | 7 | 4 | 7 | 6 | 7 | 0 |   |
| 83 | 4 | 8 | 6 | 4 | 6 | 4 | 0 | 7 | 0 |   |
| 84 | 3 | 7 | 6 | 0 | 6 | 5 | 0 | 7 | 0 |   |
| 85 | 0 | 0 | 0 | 0 | 0 | 0 | 4 | 8 | 3 |   |
| 86 | 0 | 9 | 8 | 0 | 6 | 6 | 6 | 9 | 0 |   |
| 87 | 8 | 9 | 9 | 0 | 7 | 0 | 6 | 7 | 0 |   |
| 88 | 7 | 9 | 7 | 0 | 8 | 7 | 0 | 7 | 0 |   |
| 89 | 9 | 9 | 8 | 0 | 7 | 7 | 8 | 7 | 0 |   |
| 90 | 0 | 0 |   | 0 | 0 | 0 | 4 | 6 | 0 |   |
| 91 | 0 | 9 | 9 | 4 | 0 | 0 | 0 | 7 | 0 |   |
| 92 | 7 | 9 | 9 | 0 | 6 | 0 | 4 | 6 | 0 |   |
| 93 | 0 | 9 | 8 | 0 | 6 | 0 | 0 | 4 | 0 |   |
| 94 | 7 | 9 | 8 | 6 | 4 | 0 | 0 | 0 | 0 |   |
| 95 | 7 | 9 | 9 | 0 | 0 | 0 | 4 | 0 | 0 |   |
| 96 | 6 | 0 | 6 | 0 | 0 | 0 | 0 | 0 | 0 |   |
| 97 | 7 | 9 | 9 | 9 | 4 | 7 | 4 | 0 | 0 |   |
| 98 | 6 | 9 | 8 | 0 | 6 | 0 | 5 | 8 | 0 |   |
| 99 | 9 | 9 | 7 | 7 | 8 | 8 | 0 | 0 | 0 |   |
| 100 | 7 | 9 | 7 | 0 | 9 | 8 | 0 | 8 | 0 |   |
| 101 | 0 | 4 |   | 0 | 7 | 0 | 0 | 8 | 0 |   |
| 102 | 0 | 9 | 8 | 0 | 4 | 0 | 0 | 6 | 0 |   |
| 103 | 0 | 6 |   | 0 | 0 | 0 | 0 | 8 | 0 |   |
| 104 | 0 | 8 | 8 | 0 | 0 | 0 | 0 | 5 | 0 |   |
| 105 | 6 | 9 | 0 | 0 | 8 | 7 | 0 | 0 | 0 |   |
| 106 | 0 | 8 |   | 0 | 5 | 0 | 5 | 4 | 2 |   |
| 107 | 4 | 5 |   | 0 | 0 | 6 | 6 | 6 | 0 |   |
| 108 | 0 |   | 4 | 0 | 0 | 0 | 2 | 5 | 0 |   |
| 109 | 3 | 7 |   | 6 | 0 | 7 | 4 | 7 | 0 |   |
| 110 | 0 | 9 | 3 | 8 | 0 | 5 | 8 | 5 | 0 |   |
| 111 | 6 | 0 |   | 5 | 0 | 5 | 7 | 6 | 0 |   |
| 112 | 0 | 0 |   | 0 | 0 | 4 | 0 | 4 | 0 |   |
| 113 | 0 | 9 | 6 | 5 | 7 | 6 | 4 | 1 | 0 |   |
| 114 | 5 | 9 | 7 | 0 | 0 | 0 | 2 | 0 | 0 |   |
| 115 | 0 | 9 | 3 | 0 | 0 | 3 | 0 | 2 | 0 |   |
| 116 | 0 | 0 |   | 6 | 0 | 3 | 0 | 3 | 0 |   |
| 117 | 6 | 9 | 7 | 5 | 5 | 7 | 8 | 6 | 0 |   |
| 118 | 0 | 7 | 3 | 0 | 6 | 6 | 0 | 5 | 0 |   |
| 119 | 7 | 0 |   | 0 | 0 | 4 | 0 | 6 | 0 |   |
| 120 | 1 | 0 |   | 0 | 4 | 0 | 0 | 4 | 0 |   |
| 121 | 1 | 0 |   | 0 | 0 | 4 | 0 | 4 | 0 |   |
| 122 | 0 | 3 |   | 1 | 0 | 0 | 0 | 0 | 0 |   |
| 123 | 7 | 0 |   | 0 | 6 | 4 | 0 | 6 | 1 |   |
| 124 | 7 | 9 | 7 | 8 | 6 | 5 | 4 | 7 | 0 |   |
| 125 | 6 | 0 |   | 0 | 6 | 6 | 0 | 5 | 0 |   |
| 126 | 4 | 0 |   | 0 | 4 | 6 | 0 | 5 | 0 |   |
| 127 | 8 | 9 | 9 | 8 | 0 | 0 | 0 | 6 | 0 |   |
| 128 | 8 | 9 | 9 | 0 | 6 | 0 | 3 | 0 | 0 |   |
| 129 | 7 | 6 |   | 0 | 0 | 0 | 0 | 0 | 0 |   |
| 130 | 0 | 7 | 7 | 0 | 8 | 4 | 0 | 0 | 0 |   |

We claim:

1. A method for the preparation of a 2,5-dioxo-3-pyrroline-1-acetic acid compound having the structural formula

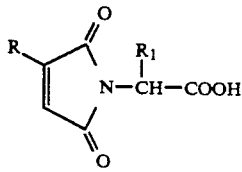

wherein
  R is hydrogen, halogen or $C_1$-$C_4$ alkyl optionally substituted with halogen;
  $R_1$ is hydrogen,
    $C_1$-$C_{10}$ alkyl optionally substituted with $C_1$-$C_9$ alkoxy or halogen,
    $C_3$-$C_6$ cycloalkyl,
    $C_2$-$C_{10}$ alkylthioalkyl,
    $C_4$-$C_{10}$ cycloalkylalkyl, or phenyl or $C_7$-$C_{10}$ phenylalkyl optionally substituted
      with one to three halogen atoms, $C_1$-$C_4$ alkoxy groups, nitro groups, cyano groups, or $C_1$-$C_4$ alkyl groups optionally substituted with halogen;
when $R_1$ is a substituent other than hydrogen, the optical isomers thereof which comprises reacting an amino acid compound having the structural formula

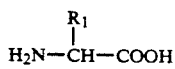

wherein $R_1$ is as described above with at least one molar equivalent of a maleic anhydride compound having the structural formula

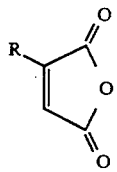

wherein R is as described above in the presence of a carboxylic acid and a polar solvent to form a N-(carboxymethyl)maleamic acid compound having the structural formula

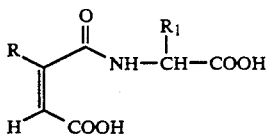

wherein R and $R^1$ are as described above and heating the N-(carboxymethyl)maleamic acid compound in the presence of at least two molar equivalents of an amine base and an azeotropic organic solvent with the azeotropic removal of water to form the corresponding 2,5-dioxo-3-pyrroline- 1-acetate and admixing the 2,5-dioxo-3-pyrroline-1-acetate with at least one molar equivalent of an aqueous mineral acid to form said 2,5-dioxo-3-pyrroline-1-acetic acid compound.

2. The method according to claim 1 wherein the carboxylic acid is acetic acid, formic acid, propionic acid or butyric acid.

3. The method according to claim 2 wherein the carboxylic acid is acetic acid.

4. The method according to claim 1 wherein the polar solvent is acetone, methyl isobutyl acetone, or acetonitrile.

5. The method according to claim 4 wherein the polar solvent is acetone.

6. The method according to claim 1 wherein the amine base is a secondary amine base, tertiary amine base or an aromatic amine base.

7. The method according to claim 6 wherein the amine base is a tertiary amine base.

8. The method according to claim 7 wherein the amine base is triethylamine.

9. The method according to claim 1 wherein the azeotropic organic solvent is benzene, toulene, or xylene.

10. The method according to claim 9 wherein the azeotropic organic solvent is toulene.

11. The method according to claim 1 wherein the aqueous mineral acid is aqueous hydrochloric acid.

* * * * *